United States Patent
Mejia

(10) Patent No.: US 11,166,835 B2
(45) Date of Patent: Nov. 9, 2021

(54) RHINOPLASTY APPLIANCE AND METHOD OF FORMING THE SAME

(71) Applicant: Martha L. Mejia, Doral, FL (US)

(72) Inventor: Martha L. Mejia, Doral, FL (US)

( * ) Notice: Subject to any disclaimer, the term of this patent is extended or adjusted under 35 U.S.C. 154(b) by 370 days.

(21) Appl. No.: 16/367,923

(22) Filed: Mar. 28, 2019

(65) Prior Publication Data
US 2019/0282390 A1 Sep. 19, 2019

Related U.S. Application Data

(63) Continuation of application No. 14/317,840, filed on Jun. 27, 2014, now abandoned.

(60) Provisional application No. 61/841,504, filed on Jul. 1, 2013.

(51) Int. Cl.
| | |
|---|---|
| *A61F 5/08* | (2006.01) |
| *B29C 39/10* | (2006.01) |
| *B29L 31/00* | (2006.01) |
| *B29K 33/00* | (2006.01) |
| *B29K 305/12* | (2006.01) |

(52) U.S. Cl.
CPC .............. *A61F 5/08* (2013.01); *B29C 39/10* (2013.01); *B29K 2033/08* (2013.01); *B29K 2305/12* (2013.01); *B29L 2031/753* (2013.01)

(58) Field of Classification Search
CPC ....... A61F 5/08; B29C 39/10; B29K 2305/12; B29K 2033/08; B29L 2031/753
See application file for complete search history.

(56) References Cited

U.S. PATENT DOCUMENTS

| | | | | |
|---|---|---|---|---|
| 2,672,138 A | | 3/1954 | Carlock | |
| 4,221,217 A | * | 9/1980 | Amezcua | A62B 23/06 128/203.22 |
| 5,533,506 A | * | 7/1996 | Wood | A61M 16/0666 128/207.18 |
| 5,775,335 A | * | 7/1998 | Seal | A62B 23/06 128/204.12 |

(Continued)

OTHER PUBLICATIONS

Cenzi, R. et al. "A dynamic nostril splint in the surgery of the nasal tip: technical innovation" *Journal of Cranio-Maxillofacial Surgery*, 1996, pp. 88-91, vol. 24, No. 2.

(Continued)

*Primary Examiner* — Phong Son H Dang
(74) *Attorney, Agent, or Firm* — Saliwanchik, Lloyd & Eisenschenk

(57) ABSTRACT

A rhinoplasty appliance is provided that may be custom-molded to a patient's nasal anatomy, including the nostrils, to maintain the corrected contour of the nostrils after rhinoplastic surgery. The rhinoplasty appliance may include a support wire; a first and second wire flanges; a first and second nostril insertion portions, each having a passage and an aperture to permit flow of air and drainage; a connecting structure to maintain the position of the nostril insertion portions in relation to each other, and to provide support and protection for the columella. The first and second wire flange may help to secure the rhinoplasty appliance in position on the patient's face, and improve retention of the first and second nostril insertion portions in the patient's nostrils. The support wire may be provided as added support for the connecting structure.

9 Claims, 4 Drawing Sheets

(56) References Cited

U.S. PATENT DOCUMENTS

| | | | | |
|---|---|---|---|---|
| 5,895,409 | A * | 4/1999 | Mehdizadeh | A61F 5/08 606/199 |
| 6,004,342 | A * | 12/1999 | Filis | A61F 5/08 606/199 |
| 6,216,694 | B1 * | 4/2001 | Chen | A62B 23/06 128/205.27 |
| 6,270,512 | B1 * | 8/2001 | Rittmann | A61F 5/08 128/207.18 |
| 6,561,188 | B1 * | 5/2003 | Ellis | A61M 3/0262 128/203.22 |
| 6,564,800 | B1 * | 5/2003 | Olivares | A61F 5/08 128/200.24 |
| 6,978,781 | B1 * | 12/2005 | Jordan | A61F 5/08 128/206.11 |
| 7,055,523 | B1 * | 6/2006 | Brown | A61F 5/08 128/206.11 |
| 8,235,051 | B2 * | 8/2012 | Soderberg | A61F 5/56 128/848 |
| 8,322,340 | B2 * | 12/2012 | Talmon | A62B 23/06 128/206.11 |
| 9,004,071 | B2 | 4/2015 | Alexander et al. | |
| 2003/0195552 | A1 * | 10/2003 | Santin | A61F 5/08 606/199 |
| 2004/0059368 | A1 * | 3/2004 | Maryanka | A61M 29/00 606/191 |
| 2004/0147954 | A1 * | 7/2004 | Wood | A61M 29/00 606/199 |
| 2004/0237967 | A1 * | 12/2004 | Davis | A61F 5/08 128/207.18 |
| 2005/0066972 | A1 * | 3/2005 | Michaels | A62B 23/06 128/206.11 |
| 2005/0094091 | A1 * | 5/2005 | Hsu | G02C 1/02 351/110 |
| 2006/0085027 | A1 | 4/2006 | Santin et al. | |
| 2007/0107731 | A1 | 5/2007 | Reed | |
| 2007/0219575 | A1 | 9/2007 | Mejia | |
| 2008/0053448 | A1 * | 3/2008 | Liska | A62B 23/06 128/206.11 |
| 2008/0097517 | A1 * | 4/2008 | Holmes | A61F 5/08 606/199 |
| 2009/0234383 | A1 * | 9/2009 | Ierulli | A61F 5/08 606/204.45 |
| 2009/0248058 | A1 | 10/2009 | Kotler | |
| 2009/0272386 | A1 * | 11/2009 | Kurtz | A61F 5/56 128/848 |
| 2009/0277459 | A1 | 11/2009 | Al-Zeir | |
| 2009/0301499 | A1 * | 12/2009 | Chalk | A61F 5/56 128/848 |
| 2011/0093004 | A1 * | 4/2011 | Ierulli | A61F 5/08 606/204.45 |
| 2013/0092173 | A1 * | 4/2013 | Alexander | A61B 1/00066 128/207.18 |
| 2013/0118488 | A1 * | 5/2013 | Ledogar | A61M 15/085 128/203.12 |
| 2014/0246023 | A1 * | 9/2014 | Maryanka | A61B 17/24 128/203.22 |
| 2014/0261459 | A1 | 9/2014 | Santelli, Jr. | |
| 2015/0196420 | A1 * | 7/2015 | Ede | A61M 29/00 604/285 |
| 2015/0230965 | A1 * | 8/2015 | Weir | A61F 5/08 606/204.45 |
| 2015/0272770 | A1 * | 10/2015 | Hopper | A61F 5/08 606/199 |
| 2016/0120689 | A1 * | 5/2016 | Bende | A61M 29/00 606/199 |

OTHER PUBLICATIONS

Costa, P. et al. "An Expansible splint for treatment of nostril stenosis" *Ann Plast Surg.*, Feb. 1995, pp. 197-200, vol. 34, No. 2.

Ramstad, T. et al. "Nasal Stenosis after Operations on the Nose: Expansion and Subsequent Maintenance of the Nasal Airway. Case Report" *Scand J Plast Reconstr Surg Hand Surg.*, Sep. 1994, pp. 235-238, vol. 28, No. 3.

* cited by examiner

RHINOPLASTY APPLIANCE AND METHOD OF FORMING THE SAME

CROSS-REFERENCE TO RELATED APPLICATIONS

This application is a continuation of U.S. application Ser. No. 14/317,840, filed Jun. 27, 2014, which claims the benefit of U.S. provisional application Ser. No. 61/841,504, filed Jul. 1, 2013, the disclosures of which are hereby incorporated by reference in their entireties.

BACKGROUND

Cleft palate is one of the most common craniofacial disorders, with a prevalence of 1/700 live births. Craniofacial problems are not only of skeletal nature, but may also involve musculature and soft tissue.

Clinicians, particularly plastic surgeons, face difficulties in maintaining the corrected shape and size of the human nostril following surgery in patients with cleft lip and/or palate, cranio-facial abnormalities and the like. For example, the forces of scar contracture may lead to stenotic nostrils. In many such cases, after surgery, a nasal stent of a fixed size dependent on the patient's specific measurements and nostril configuration may be inserted and retained in the nasal cavity.

Previously, round tubes were used following surgery to resist nasal stenosis. However, such round tubes have proven unsuitable aesthetically because they promote healing of the nostril with a round shape, which is unappealing since the normal nostril shape is not truly round.

To address this problem, soft silicone rubber stents, tubes or scaffolds have been specifically made for the human nostril shape. These stents tend to easily fall out or be extruded in use, particularly in children. They may be retained in proper placement with transseptal sutures, but sutures may be uncomfortable or may have complications. Even with the use of suture retention, these stents typically are not retained in place in children for longer than a few weeks. Additionally, cases have been reported where the transseptal sutures have cut through the columella.

Therefore, there is currently an unmet need for a rhinoplasty appliance for use after surgery that protects the columella and nasal nostrils while improving and maintaining the desired shape and form of the nasal nostril. It is also desirable to provide such a rhinoplasty appliance that is more comfortable, easy to make, and not easily extruded when in use.

BRIEF SUMMARY

The subject invention provides a rhinoplasty appliance that is custom-molded to a patient's nasal nostrils to maintain the corrected contour of the nostrils after rhinoplastic surgery. The subject invention further provides methods of using the rhinoplasty appliance. The rhinoplasty appliance is, advantageously, easy and inexpensive to manufacture from readily available materials, such as metals and thermoplastic materials.

In a specific embodiment, a rhinoplasty appliance which may be removably inserted within the nostrils of a patient may have a first and second nostril insertion portions, a connecting structure, and a first and second flange. The nostril insertion portions may each have a passage and an aperture to permit flow of air and drainage. The connecting structure may couple the first and second nostril insertion portions to each other. The first flange may be affixed to the first nostril insertion portion, and the second flange may be affixed to the second nostril insertion portion. The first and second flanges may each have a fastener.

The first and second nostril insertion portions and the connecting structure may be integrally molded of a thermoplastic material. The first and second nostril insertion portions and the connecting structure may be customized to fit the patient's nostrils. The connecting structure may also have a support wire, which may be stainless steel. The first and second flanges may be made of resilient material, which may also be stainless steel. The fastener may be, for example, a loop, a hook, or at least one adhesive. The rhinoplasty appliance may also have a therapeutic agent. The apertures of the first and second nostril insertion portions may have an elliptical shape. At least one cannula may be inserted through an aperture and extend into a passage.

The subject invention includes methods for maintaining the patency of nostril structure following corrective surgery. In one such method, a rhinoplasty appliance may be formed by making an impression of the nasal cavity of a patient; forming a mold from the impression, including a first and second nasal nostrils and a columella; placing a liquid resin mix within the first and second nasal nostrils and around the columella of the mold; inserting a support wire, a first and second flanges, and a first and second aperture spacers into the resin mix before the mix sets; and after the mix sets, removing the first and second aperture spacers. The resin mix may be a thermoplastic acrylic resin.

In another method, a rhinoplasty appliance may be provided to a patient, a first and second nostril insertion portions may be inserted into the patient's nostrils; the first and second wire flanges may be retained in position on the patient's face; and the rhinoplasty appliance may be worn to maintain at least one nostril structure. The patient may be a human baby, infant, child, adolescent, or adult. The rhinoplasty appliance may be worn continuously for about two to three months following corrective surgery. After wearing the rhinoplasty appliance continuously for about two to three months, the rhinoplasty appliance may be worn at night for about four to six months. The first and second flanges may be retained on the patient's face using elastic bands or adhesive.

BRIEF DESCRIPTION OF DRAWINGS

In order that a more precise understanding of the above-recited invention can be obtained, a more particular description of the invention briefly described above will be rendered by reference to specific embodiments thereof that are illustrated in the appended drawings. The drawings presented herein may not be drawn to scale and any reference or implication of dimensions in the drawings or the following description are specific to the embodiments disclosed. Any variations of these dimensions that will allow the subject invention to function for its intended purpose are within the scope of the subject invention. Thus, these drawings depict only specific embodiments of the invention and are not limiting in scope.

DETAILED DISCLOSURE

Figure 1:
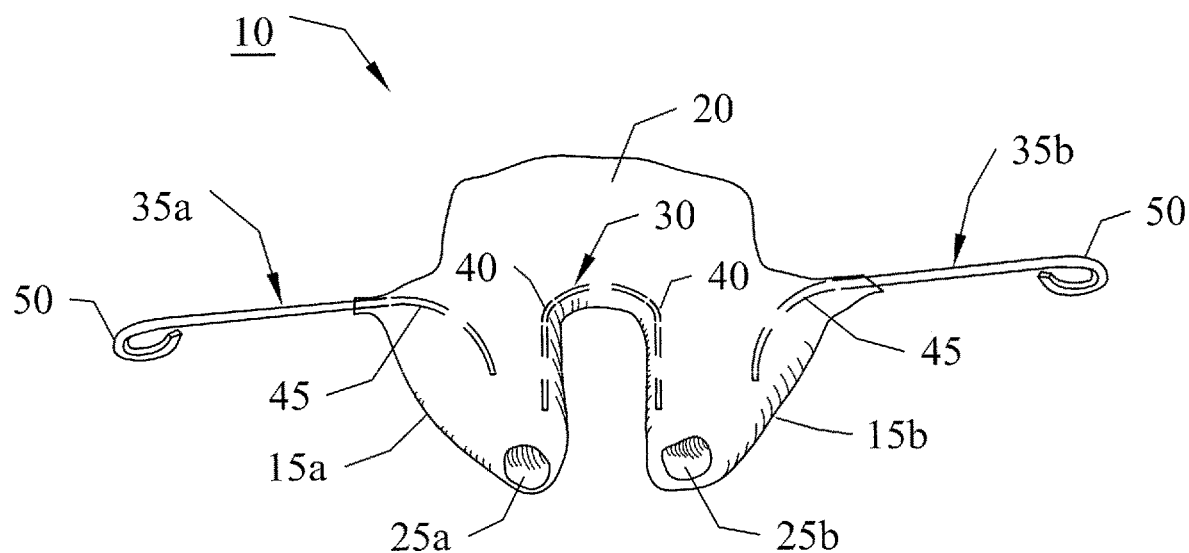
FIG. 1 shows a top perspective view of an embodiment of the subject invention.

The term "patient" as used herein, refers to a mammal, preferably a human, to which the present invention is applied. Those that can benefit from the disclosed rhinoplasty appliance include, but are not limited to, neonates, infants, children, adolescents and adults.

References to "first", "second", and the like (e.g., first and second securing wire), as used herein, and unless otherwise specifically stated, are intended to identify a particular feature of which there are at least two. However, these references are not intended to confer any order in time, structural orientation, or sidedness (e.g., left or right) with respect to a particular feature.

With reference to the drawings wherein like reference characters designate like or corresponding elements throughout the several views, it will be seen that the invention comprises a rhinoplasty appliance shown generally at 10.

In the embodiment shown in FIG. 1, a rhinoplasty appliance 10 comprises a first and second nostril insertion portions 15a, 15b and a connecting structure 20, all of which are preferably integrally molded from an elastomeric and/or thermoplastic material (e.g., silicone, rubber, plastic). Preferably, the thermoplastic material is an acrylic resin. Even more preferably, the acrylic resin is derived from an orthodontic resin powder and liquid as more fully described later herein.

The first and second insertion portions 15a, 15b are generally identical in shape and size and each include a passage and an aperture 25a, 25b to ensure air flow and drainage when in use. The first and second insertion portions 15a, 15b are custom formed to fit within the nostrils of the patient and conform to the internal shape thereof. In certain embodiments, the first and second insertion portions are roughly between about 1 to 25 mm in length, more preferably about 3 to 15 mm in length; and roughly between about 1 to 15 mm in diameter, more preferably about 3 to 7 mm in diameter. As understood by the skilled artisan, the size and shape of the first and second insertion portions are customized to the patient and the lengths and diameters of the insertion portions will vary.

The connecting structure 20 comprises a support wire 30. The first and second insertion portions 15a, 15b each comprise wire flanges 35a, 35b. The support wire 30 and the wire flanges 35a, 35b may be made of resilient, semi-rigid or rigid material (e.g., metal). Preferably, the support wire 30 and the wire flanges 35a, 35b can be made of stainless steel. The diameter of the stainless steel wire is about 0.5 mm to about 1.5 mm, more preferably approximately 0.9 mm.

The support wire 30 is formed with a series of bends 40 in order to anchor the same firmly within the connecting structure 20 while it sets. The wire flanges 35a, 35b are formed with bends 45 at the proximal ends to anchor the same within the insertion portions 15a, 15b. The distal ends of the wire flanges 35a, 35b terminate in a small loop or hook 50 to assist in securing the appliance 10 to the patient and to avoid a sharp end which could cut or damage the patient or surgeon.

Figure 2:
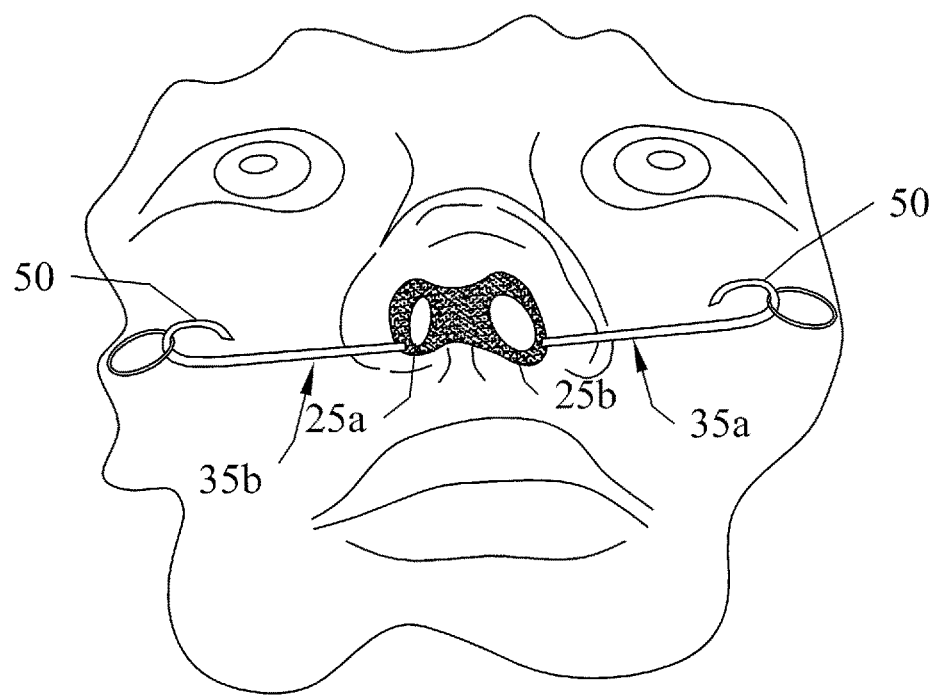
FIG. 2 shows a front view of a portion of the face of a typical patient with the embodiment of FIG. 1 inserted and retained in place in the patient's nostrils.

As illustrated in FIG. 2, the first and second insertion portions 15a, 15b are formed to fit within the nostrils of the patient. In certain embodiments, adhesives are placed at the distal ends of the wire flanges 35a, 35b to secure the appliance 10 to the patient's face and prevent withdrawal or expulsion of the insertion portions 15a, 15b from the patient's nostrils. In addition, or alternatively, one or more elastic bands are placed in the loops 50 to assist securing the appliance 10 to the patient's face. In a related embodiment, a single elastic band may be used to connect the distal ends of the wire flanges 35a, 35b to secure the appliance to the patient's head. As understood by the skilled artisan, due to differences in patient faces, the lengths of the wire flanges will vary to ensure proper fixation to the patient's face The rhinoplasty appliance can further comprise a therapeutic agent. Therapeutic agents may be incorporated in the appliance or may be provided on the surface of the appliance. Examples of therapeutic agents include, but are not limited to, antibiotics and other medications.

Proper fit and retention is very important since the rhinoplasty appliance may be worn for many months both at night and during the day. To enhance patient comfort and fit of the rhinoplasty appliance, several of the most likely sizes and dimensions may be made in advance, or the rhinoplasty appliance may be individually customized to each patient. Some examples may include providing rhinoplasty appliances having more than one range of sizes, which may roughly correspond to patients who may be characterized as neonatal, pediatric, or adolescent. In a first specific example, a neonatal rhinoplasty appliance may have a length of approximately 8-10 mm, a height of approximately 5-7 mm, and a width of approximately 4-5 mm. In a second specific example, a pediatric rhinoplasty appliance may have a length of approximately 10-12 mm, a height of approximately 8-10 mm, and a width of approximately 6 mm. In a third specific example, an adolescent rhinoplasty appliance may have a length of approximately 10-15 mm, a height of approximately 11-13 mm, and a width of approximately 7 mm. All of the dimensions of each specific example may be adjusted by a millimeter or more to better fit the patient's anatomy.

The rhinoplasty appliance described above is of primary importance in restoring the nostril size and shape, especially for patients with cleft lip or crania-facial anomalies. With conventional nasal stents, the same are used for no more than one week post surgery and in many cases, the nasal tissue may collapse and will not permit optimal aesthetic results.

The rhinoplasty appliance may also be used with patients requiring a nasal cannula, such as a medical tube providing oxygen. The appliance may be used to protect the columnella during insertion of a cannula through an aperture and extending into a passage.

Figure 3:
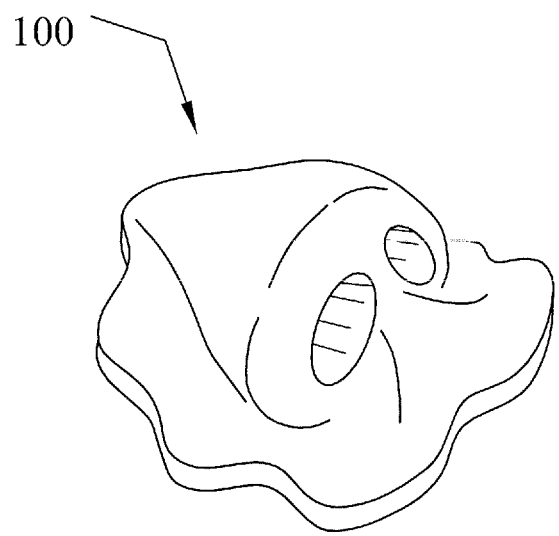
FIG. 3 shows a mold from a patient's nose.
Figure 4:
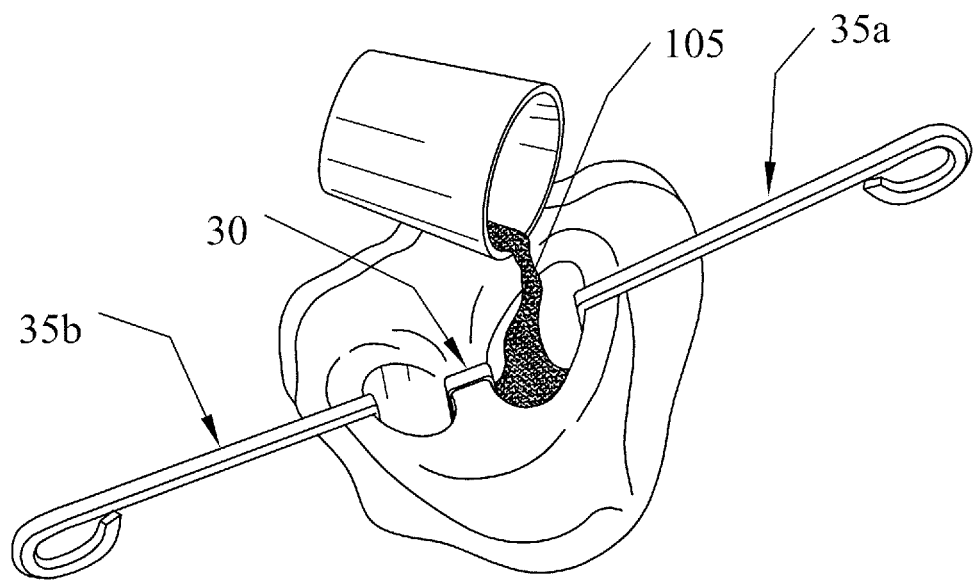
FIG. 4 shows the manner of pouring the resin mix from which the embodiment of FIG. 1 is formed.

In order to custom-form the rhinoplasty appliance, an impression of the patient's nose is taken using any orthodontic or similar mold casting material, see FIG. 3. The resulting mold 100 serves as a reservoir into which a mixture of orthodontic resin powder and liquid 105 may be poured as shown in FIG. 4. Specifically, the mold provides an impression of the patient's nostrils and columella to which the resin mixture is applied.

Figure 5:
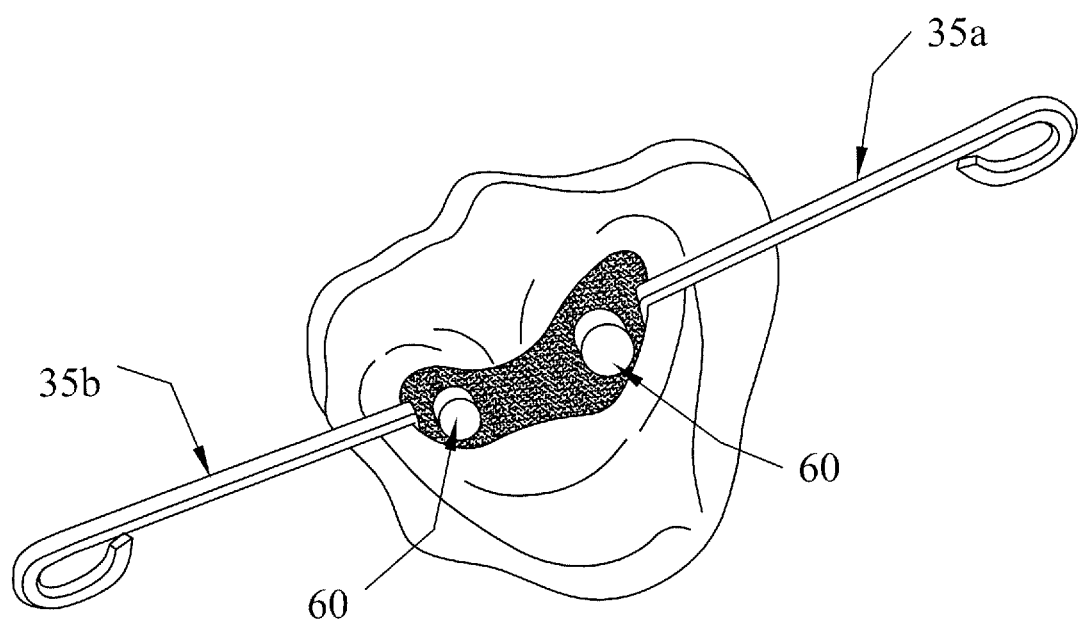
FIG. 5 shows an exploded perspective view of the mold of FIG. 4.
Figure 6:
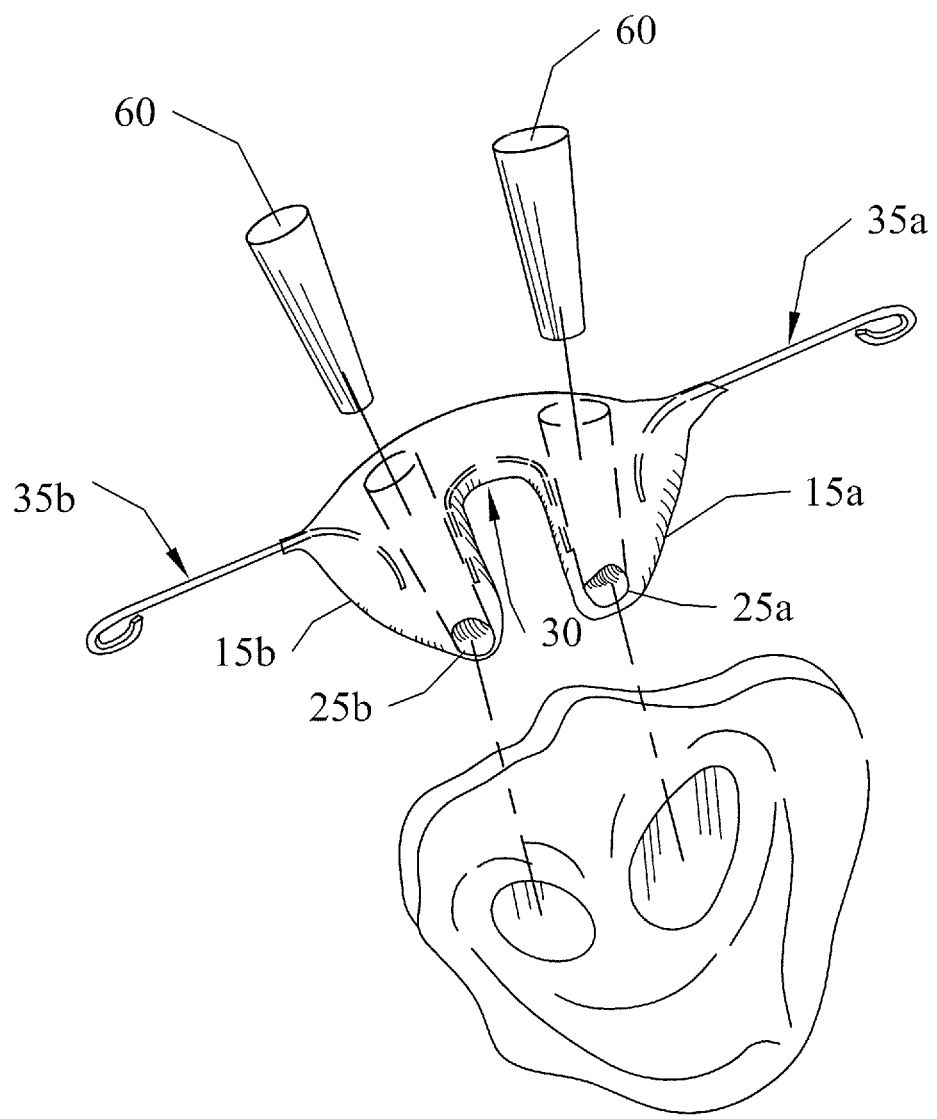
FIG. 6 shows an exploded view of the embodiment of FIG. 1 once set and removed from the mold of FIG. 5.

Before the resin mix is poured into the mold or before the resin mix sets, a support wire 30, wire flanges 35a, 35b and aperture spacers 60 are inserted in the mold, see FIG. 5. Aperture spacers 60 are employed to ensure a passage and opening are formed in the nostril insertion portions 15a, 15b to permit flow of air and drainage. Once the resin mix is set, the entire assembly is removed from the mold as shown in FIG. 6 and the spacers 60 may be removed.

To maintain the patency of nostril structure following surgery, the subject rhinoplasty appliance is provided. The nostril insertion portions are inserted into a patient's nostrils and the wire flanges are affixed to the patient's face following corrective surgery. During the first period of healing, the rhinoplasty appliance is used 24 hours a day. Preferably, the rhinoplasty appliance is used 24 hours a day for about two to three months. During this period, intermittent visits can be conducted with a clinician for any revisions or adjustments to the rhinoplasty appliance. Following this period, the rhinoplasty appliance is worn only at night. Preferably, the rhinoplasty appliance is worn at night for about four to six months. Because recurrence of nostril stenosis and other nostril shape abnormalities may occur, overcorrection is recommended.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

What is claimed is:

1. A rhinoplasty appliance, adapted for removable insertion within the nostrils of a patient, comprising:
    a first nostril insertion portion having a first height of between about 7 mm and about 13 mm, first width, and first exterior surface contoured to match an interior shape of a first nostril of the patient and second nostril insertion portion having a second height of between about 7 mm and about 13 mm, a second width, and second exterior surface contoured to match an interior shape of a second nostril of the patient, wherein at least one of the first height, first width, and first exterior surface is different from at least one of the second height, second width, and second exterior surface, respectively each nostril insertion portion further having an aperture that leads to a passage to permit flow of air and drainage;
    a connecting structure operably connected to and coupling the first nostril insertion portion and the second nostril insertion portion, so that, when inserted into the nostrils of the patient, the contours of the first nostril insertion portion align with the contours in the first nostril of the patient and the contours of the second nostril insertion portion align with the contours of the second nostril of the patient;
    a first flange affixed to the first nostril insertion portion that extends laterally to the first nostril insertion portion and a second flange affixed to the second nostril insertion portion that extends laterally to the second nostril insertion portion; and a fastener operably connected to the first flange and the second flange and adapted to be secured to the patient, so as to retain the first nostril insertion portion and the second nostril insertion portion relative to the contours of the respective nostrils of the patient.

2. The rhinoplasty appliance according to claim 1, wherein the first and second nostril insertion portions and the connecting structure are integrally molded of a thermoplastic material.

3. The rhinoplasty appliance according to claim 1, further comprising a support wire integral with the connecting structure.

4. The rhinoplasty appliance according to claim 3, wherein the support wire is stainless steel.

5. The rhinoplasty appliance according to claim 1, wherein the first and second flanges are made of resilient material.

6. The rhinoplasty appliance according to claim 5, wherein the first and second flanges are stainless steel.

7. The rhinoplasty appliance according to claim 1, wherein the fastener is selected from the group consisting of: a loop, a hook, and one or more adhesives.

8. The rhinoplasty appliance according to claim 1, further comprising a therapeutic agent.

9. The rhinoplasty appliance, according to claim 1, further comprising band operably connected to the fastener, where the band is configured to go around the head of the patient.

* * * * *